(12) United States Patent
Inoue (10) Patent No.: US 8,931,903 B2
(45) Date of Patent: Jan. 13, 2015

(54) OPHTHALMOLOGIC APPARATUS, CONTROL METHOD THEREFORE, AND RECORDING MEDIUM STORING METHOD

(75) Inventor: Hiroyuki Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 190 days.

(21) Appl. No.: 13/598,808

(22) Filed: Aug. 30, 2012

(65) Prior Publication Data

US 2013/0188129 A1 Jul. 25, 2013

(30) Foreign Application Priority Data

Jan. 25, 2012 (JP) ................. 2012-012845

(51) Int. Cl.
*A61B 3/10* (2006.01)

(52) U.S. Cl.
USPC .......................... 351/221; 351/246

(58) Field of Classification Search
CPC ............. A61B 1/00045; A61B 3/1025; A61B 1/0646; A61B 3/0008
USPC .................. 351/221, 246, 206, 205
See application file for complete search history.

(56) References Cited

U.S. PATENT DOCUMENTS

| | | | |
|---|---|---|---|
| 7,677,730 B2 | 3/2010 | Shimizu | |
| 8,098,278 B2 | 1/2012 | Yumikake et al. | |
| 8,388,135 B2 * | 3/2013 | Hacker et al. | ................. 351/221 |
| 2008/0212027 A1 | 9/2008 | Shimizu | |
| 2010/0110171 A1 | 5/2010 | Satake | |
| 2010/0118132 A1 | 5/2010 | Yumikake et al. | |
| 2011/0051086 A1 | 3/2011 | Takai et al. | |
| 2012/0218520 A1 | 8/2012 | Inoue | |

FOREIGN PATENT DOCUMENTS

| | | |
|---|---|---|
| CN | 101095610 A | 1/2008 |
| CN | 101254092 A | 9/2008 |
| CN | 101677761 A | 3/2010 |
| EP | 1 872 713 A1 | 1/2008 |
| JP | 2010-110392 A | 5/2010 |
| JP | 2011-156290 A | 8/2011 |

OTHER PUBLICATIONS

Sep. 3, 2014 Chinese Official Action in Chinese Patent Appln. No. 201310023529.0.

* cited by examiner

*Primary Examiner* — Hung Dang
(74) *Attorney, Agent, or Firm* — Fitzpatrick, Cella, Harper & Scinto (57) ABSTRACT

Provided is an ophthalmologic apparatus including: a first control unit which controls a scanning unit for scanning an eye to be inspected with light emitted from a light source; a memory unit which stores control information for causing the first control unit to control the scanning unit to sequentially perform a first scan and a second scan after the first scan; and a second control unit which decreases a light amount irradiating the eye to be inspected after finishing the first scan and before starting the second scan, which are performed based on the control information.

20 Claims, 9 Drawing Sheets

OPHTHALMOLOGIC APPARATUS, CONTROL METHOD THEREFORE, AND RECORDING MEDIUM STORING METHOD

BACKGROUND OF THE INVENTION

1. Field of the Invention

This disclosure relates to an ophthalmologic apparatus for performing operations such as image acquiring, an image acquiring control method as a method of controlling the ophthalmologic apparatus, and a recording medium for storing a program for causing a computer or the like to execute the control method.

2. Description of the Related Art

An ophthalmologic apparatus (ophthalmologic OCT apparatus) for acquiring a fundus tomographic image by scanning and photographing an eye to be inspected by utilizing optical interference of near infrared laser light, and a laser scanning ophthalmoscope (ophthalmologic SLO apparatus) for acquiring a fundus image by using a confocal system are known as an image acquiring apparatus (Japanese Patent Application Laid-Open No. 2010-110392). In particular, the OCT apparatus is an apparatus that can acquire a high resolution tomographic image of a sample, and has become an essential ophthalmologic apparatus in a specialty outpatient clinic for retina. The OCT apparatus is used not only for ophthalmologic apparatus but also for an endoscope, and the like.

Further, in order to support diagnosis of various diseases, a test object (for example, a fundus of the eye to be inspected) is scanned in various scan conditions (different scan patterns and different scan ranges) for photography. The OCT apparatus splits low coherent light into reference light and measuring light, scans and irradiates the test object with the measuring light, and causes interference between return light from the test object and the reference light so that a high resolution tomographic image of the test object can be acquired. Further, a specific region is scanned with the measuring light in a one-dimensional manner so that a two-dimensional tomographic image is acquired, and further the two-dimensional tomographic images are acquired repeatedly while shifting the position so that a three-dimensional image can be acquired.

In such a conventional image acquiring apparatus, the test object (for example, the fundus of the eye to be inspected) is irradiated continuously also in a time period for changing a scan pattern to the next scan pattern. This is because, in the case where the apparatus includes a first monitor for displaying a real-time observation image (moving image) before acquiring an image and a second monitor for displaying the acquired image (still image) after acquiring the image, it is preferred that the real-time observation image (moving image) can be always observed on the first monitor. In addition, the same is true in the case where the real-time observation image and the acquired image are displayed simultaneously on a single screen.

However, in an apparatus for performing repetitive inspection and measurement using various scan patterns, there occurs a new problem of the influence of irradiation light amount integrated over time on a subject because the test object is always irradiated.

SUMMARY OF THE INVENTION

In view of the above-mentioned problem, it is one of objects of this disclosure to provide an image acquiring apparatus, an image acquiring control method, a program, and a test object measuring apparatus, which can reduce a load on both a subject and an inspector. Note that, without limiting to the above-mentioned object, to obtain action and effect derived from each of configurations described later for embodying the invention as action and effect that cannot be obtained by the conventional technology is also regarded as one of the objects of this disclosure.

In order to achieve the above-mentioned object, an ophthalmologic apparatus of this disclosure includes: a first control unit which controls a scanning unit for scanning an eye to be inspected with light emitted from a light source; a memory unit which stores control information for causing the first control unit to control the scanning unit to sequentially perform a first scan and a second scan after the first scan; and a second control unit which decreases a light amount irradiating the eye to be inspected after finishing the first scan and before starting the second scan, which are performed based on the control information.

According to this disclosure, it is possible to provide an image acquiring apparatus, an image acquiring control method, a program, and a test object measuring apparatus, which can reduce a load on both a subject and an inspector. In other words, the light amount irradiating the subject can be decreased automatically after photography.

Further features of the present invention will become apparent from the following description of exemplary embodiments with reference to the attached drawings.

BRIEF DESCRIPTION OF THE DRAWINGS

FIGS. 3A, 3B, and 3C are explanatory diagrams of operational flows according to a modified example of the first embodiment.

FIGS. 4A and 4B are related to an ophthalmologic apparatus according to a second embodiment.

DESCRIPTION OF THE EMBODIMENTS

Preferred embodiments of the present invention will now be described in detail in accordance with the accompanying drawings.

First Embodiment (Configuration of Main Body)

Figure 2A:
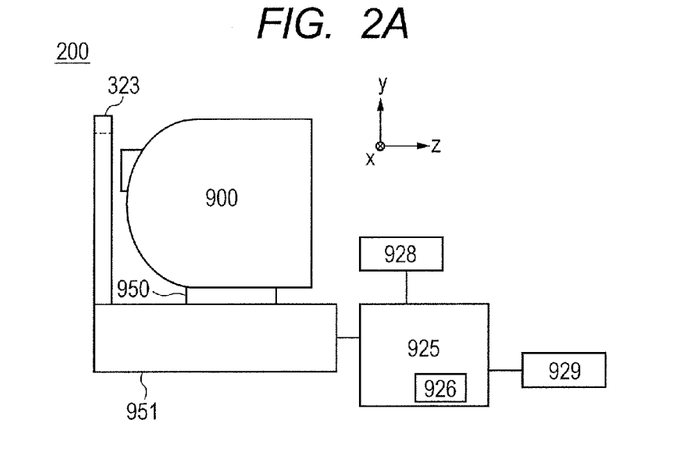
FIG. 2A is an overall schematic diagram of the ophthalmologic apparatus according to the first embodiment.

FIG. 2A is a side view of an ophthalmologic apparatus as a test object measuring apparatus according to a first embodiment. Reference numeral 200 denotes an ophthalmologic apparatus; 900, an acquiring portion (measurement optical system) for acquiring an anterior segment image as well as a two-dimensional image and a tomographic image of a fundus; and 950, a stage portion as a moving portion that can move the image acquiring portion 900 in X, Y, and Z directions using motors (not shown). Reference numeral 951 denotes a base portion in which a spectroscope described later is contained.

As described later in detail, the image acquiring portion 900 scans a test object with light for acquiring an image of the test object so as to photograph the test object and thereby acquire the image of the test object, and performs this process sequentially and repeatedly in different scan conditions, namely in a first scan condition and next in a second scan condition, for example.

Reference numeral 925 denotes a personal computer that works as both a control portion for the stage portion and an alignment control unit. The personal computer 925 performs control of the stage portion and alignment operation, and further constitutes the tomographic image described later. Reference numeral 926 denotes a hard disk that works also as a subject information storage portion, and is a storage portion for storing in advance a program for photographing tomographic images as well as the scan conditions having a predetermined order as an inspection set (that functions as measurement information indicating the order to perform the plurality of scan conditions).

Reference numeral 928 denotes a monitor as a display portion, and reference numeral 929 denotes an input portion by which an instruction to the personal computer is input and which is specifically constituted of a keyboard and a mouse. In other words, the monitor 928 is a single and common monitor for displaying a capture screen before measurement and a confirmation screen after the measurement in a time-sharing manner as described later, which is disposed not in the image acquiring portion 900 but in the personal computer 925.

Reference numeral 323 denotes a face rest including a chin rest 324 and a forehead rest 325 that can be moved up and down by motors (not shown) and an eye height line 326 disposed at the middle in the height direction of a moving area of an objective lens described later. The chin of a subject is placed on the chin rest 324, the forehead of the subject is brought into contact with the forehead rest 325, and the face of the subject is settled so that the height of the eye of the subject becomes substantially the same as the height of the eye height line 326. Thus, the eye to be inspected can be substantially positioned to the acquiring portion 900.

(Configurations of Measurement Optical System and Spectroscope)

Figure 2B:
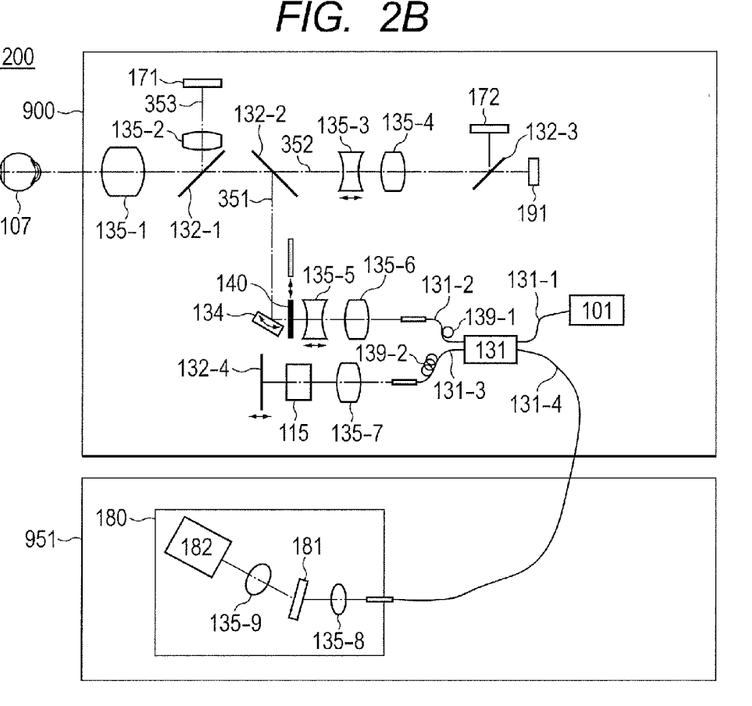
FIG. 2B is an explanatory diagram of a measurement optical system as an image acquiring portion of the ophthalmologic apparatus according to the first embodiment.

Configurations of the measurement optical system and a spectroscope of this embodiment are described with reference to FIG. 2B. First, an inside of the acquiring portion 900 is described. An objective lens 135-1 is disposed to be opposed to an eye to be inspected 107. On the optical axis of the objective lens 135-1, a first dichroic mirror 132-1 and a second dichroic mirror 132-2 are disposed. Those dichroic mirrors separate the optical path into an optical path 351 of an OCT optical system, an optical path 352 for fundus observation and a fixation lamp, and an optical path 353 for anterior segment observation in accordance with their wavelength bands.

The optical path 352 is further split by a third dichroic mirror 132-3 into an optical path to a CCD 172 for fundus observation and an optical path to a fixation lamp 191 in accordance with their wavelength bands in the same manner as described above. Here, reference numerals 135-3 and 135-4 denote lenses, and the lens 135-3 is driven by a motor (not shown) for focusing of the fixation lamp and fundus observation. The CCD 172 has a sensitivity at a wavelength of illumination light (not shown) for fundus observation, specifically at a wavelength of approximately 780 nm. On the other hand, the fixation lamp 191 generates visible light so as to prompt the subject to stare.

In the optical path 353, reference numerals 135-2 and 135-10 denote lenses; 140, a split prism; and 171, a CCD for anterior segment observation for detecting infrared light. This CCD 171 has a sensitivity at a wavelength of illumination light (not shown) for anterior segment observation, specifically at a wavelength of approximately 970 nm. The split prism 140 is disposed at a position conjugate with the pupil of the eye to be inspected 107, and hence a distance of the acquiring portion 900 in a Z direction (front and rear direction) with respect to the eye to be inspected 107 can be detected as a split image of the anterior segment.

The optical path 351 constitutes the OCT optical system as described above, and is used for photographing a tomographic image of the fundus of the eye to be inspected 107. More specifically, the optical path 351 is used for acquiring an interference signal for forming the tomographic image. Reference numeral 134 denotes an XY scanner for scanning the fundus with light. The XY scanner 134 is illustrated as a single mirror but is a galvano-mirror for scanning in two directions of X and Y axes.

Reference numerals 135-5 and 135-6 denote lenses, and the lens 135-5 is driven by a motor (not shown) so as to focus light from an OCT light source 101 emerging from a fiber 131-2 connected to an optical coupler 131 on the fundus 107. By this focusing operation, light from the fundus 107 forms images simultaneously as a spot on an end of the fiber 131-2 and enters the fiber 131-2.

Next, configurations of an optical path from the OCT light source 101, a reference optical system, and the spectroscope are described.

Reference numeral 101 denotes the OCT light source; 132-4, a reference mirror; 115, a dispersion compensating glass; 131, the optical coupler; 131-1 to 131-4, single-mode optical fibers connected and integrated to the optical coupler; 135-7, a lens; and 180, a spectroscope.

These elements constitute a Michelson interferometer. The light emitted from the OCT light source 101 passes through the optical fiber 131-1 and is split by the optical coupler 131 into measuring light on the optical fiber 131-2 side and reference light on the optical fiber 131-3 side.

The measuring light irradiates the fundus of the eye to be inspected 107 as an observation target via the above-mentioned optical path of the OCT optical system and is reflected or scattered by the retina to reach the optical coupler 131 via the same optical path.

The optical coupler 131 combines the measuring light with the reference light to be interference light. Here, the interference occurs when an optical path length of the measuring light becomes almost the same as an optical path length of the reference light. The reference mirror 132-4 is retained in an adjustable manner in an optical axis direction by a motor (not shown) and a drive mechanism (not shown), and hence the optical path length of the reference light can be adjusted to the optical path length of the measuring light that varies depending on the eye to be inspected 107. The interference light is guided to the spectroscope 180 via the optical fiber 131-4.

In addition, reference numeral 139-1 denotes a polarization adjustment portion on the measuring light side disposed in the optical fiber 131-2. Reference numeral 139-2 denotes a polarization adjustment portion on the reference light side disposed in the optical fiber 131-3. The polarization adjustment portions include some parts in which the optical fiber is looped, and the looped part is turned about a longitudinal direction of the fiber so that the fiber is twisted. Thus, polarized states of the measuring light and the reference light can be adjusted respectively to the same state.

The spectroscope 180 is formed of lenses 135-8 and 135-9, a diffraction grating 181, and a line sensor 182. The interference light emerged from the optical fiber 131-4 becomes collimated light via the lens 135-8, and is then diffracted by the diffraction grating 181 so as to form images on the line sensor 182 via the lens 135-9.

Next, a periphery of the OCT light source 101 is described. The OCT light source 101 is a super luminescent diode (SLD) that is a typical low coherent light source. The center wavelength is 855 nm, and the wavelength band width is approximately 100 nm. Here, the band width is an important parameter because it affects a resolution of the acquired tomographic image in the optical axis direction.

The SLD is selected as a type of the light source here, but it is sufficient as long as the light source can emit low coherent light. It is possible to use an amplified spontaneous emission (ASE) or the like. As to the center wavelength, near infrared light is suitable in view of measuring an eye. In addition, because the center wavelength affects the resolution of the acquired tomographic image in a lateral direction, it is desired that the wavelength be as short as possible. The center wavelength is set to 855 nm because of the both reasons.

The Michelson interferometer is used in this embodiment, but a Mach-Zehnder interferometer may be used. In accordance with a light intensity difference between the measuring light and the reference light, it is desired to use the Mach-Zehnder interferometer when the light intensity difference is large, and to use the Michelson interferometer when the light intensity difference is relatively small.

(Method of Photographing Tomographic Image)

A method of photographing the tomographic image using the ophthalmologic apparatus 200 is described. The ophthalmologic apparatus 200 can photograph the tomographic image of a predetermined part of the eye to be inspected 107 by controlling the XY scanner 134. In other words, the ophthalmologic apparatus 200 corresponds to an example of a first control unit which controls a scanning unit for scanning the eye to be inspected with light. First, measuring light scans in an X direction in the figure so that the line sensor 182 photographs information of a predetermined number of lines in a photographing range of the fundus in the X direction. The fast Fourier transform (FFT) is performed on a luminance distribution on the line sensor 182 obtained at a certain position in the X direction, and information obtained by the FFT from the linear luminance distribution is converted into density or color information to be displayed on the monitor 928. This converted information is referred to as an A-scan image.

In addition, a two-dimensional image on which a plurality of A-scan images is arranged is referred to as a B-scan image. After a plurality of A-scan images is photographed for constructing one B-scan image, the scan value in a Y direction is moved, and the scanning in the X direction is performed again so that a plurality of B-scan images is acquired.

The plurality of B-scan images or a three-dimensional image constructed from the multiple B-scan images is displayed on the monitor 928 described below so as to be used for diagnosis of the eye to be inspected by the inspector.

(Capture Screen Displayed on Monitor Before Photography)

Figure 1A:
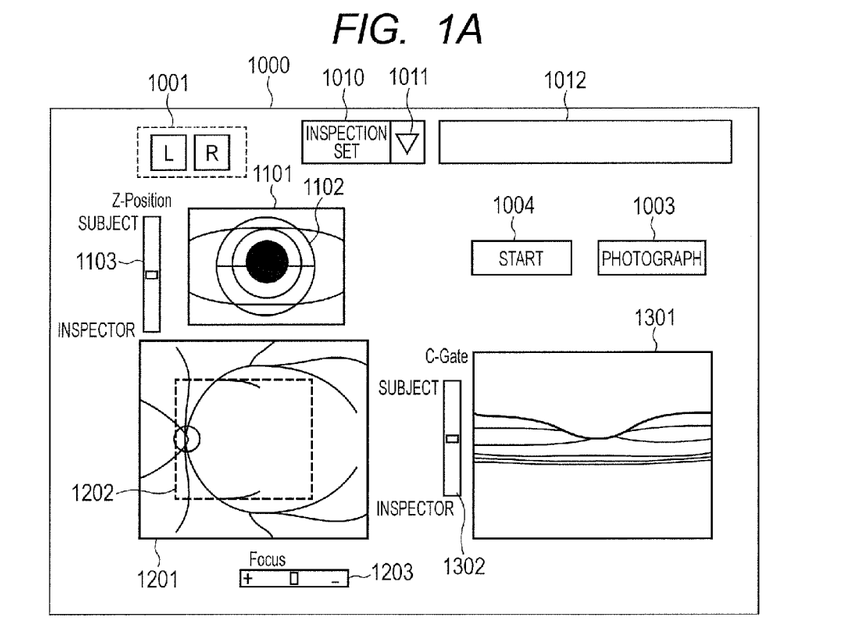
FIG. 1A is an explanatory diagram of a capture screen for displaying a real-time image (moving image) before photography in an ophthalmologic apparatus according to a first embodiment.

With reference to FIG. 1A, the capture screen according to this embodiment is described. The capture screen is a screen for performing various settings and adjustments so as to acquire a desired image of the eye to be inspected, and is a screen displayed on the monitor before photography. Reference numeral 1101 denotes an observation screen for the anterior segment obtained by the anterior segment observation CCD 171; 1201, a display screen for a two-dimensional fundus image obtained by the fundus observation CCD 172; and 1301, a tomographic image display screen for checking the acquired tomographic image. Reference numeral 1001 denotes buttons for switching between both eyes to be inspected. When an L button or an R button is pressed, the acquiring portion 900 is moved to an initial position for the left or right eye.

Reference numeral 1010 denotes an inspection set selection screen, which displays the selected inspection set. In order to change the inspection set, the inspector clicks 1011 so as to display a pull-down menu (not shown) and selects a desired inspection set. In addition, a scan pattern display screen 1012 displays an outline of the scan pattern performed by the currently selected inspection set, for example, a horizontal scan, a vertical scan, a cross scan, and the like.

When an arbitrary point on the anterior segment observation screen 1101 is clicked by the mouse, the acquiring portion 900 is moved so that the point becomes a center of the screen. Thus, alignment between the acquiring portion and the eye to be inspected is performed.

Reference numeral 1004 denotes a start button. When this button is pressed, acquiring of the two-dimensional image and the tomographic image is started. The acquired images of the eye to be inspected are displayed in real time on the two-dimensional image display screen 1201 and the tomographic image display screen 1301. A slider disposed in the vicinity of each of the images is used for adjustment. A slider 1103 is used for adjusting a position of the acquiring portion in the Z direction with respect to the eye to be inspected, a slider 1203 is used for focus adjustment, and a slider 1302 is used for adjusting a coherence gate position.

The focus adjustment is an adjustment of moving the lenses 135-3 and 135-5 in the illustrated arrow directions so as to adjust focus on the fundus. The coherence gate adjustment is an adjustment of moving the reference mirror 132-4 in the illustrated direction so that the tomographic image is observed at a desired position on the tomographic image display screen. By these adjustment operations, the inspector can create a state where an optimal photography can be performed. Reference numeral 1003 denotes a photography button, which is pressed for performing a desired photography after various adjustments are completed.

(Configuration of Tomographic Image Confirmation Screen)

Figure 1B:
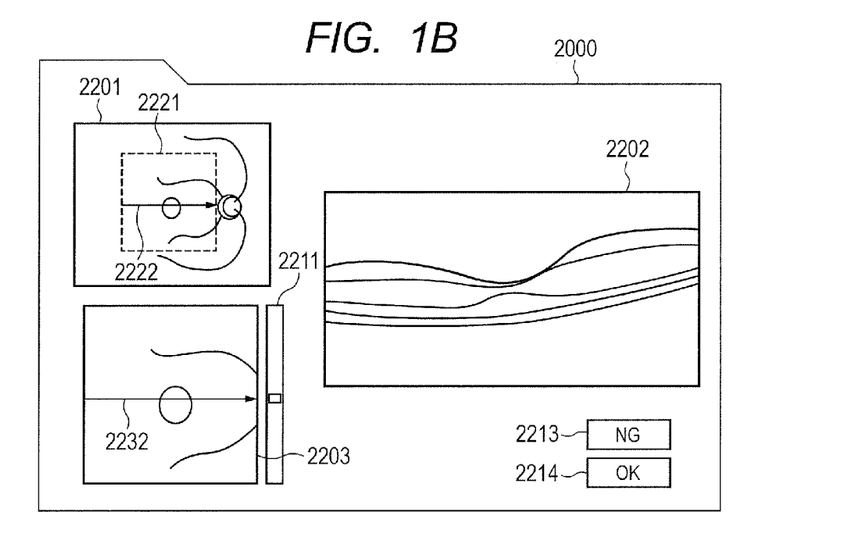
FIG. 1B is an explanatory diagram of a confirmation screen for displaying a still image after the photography on the same monitor.

Next, with reference to FIG. 1B, a confirmation screen 2000 according to this embodiment is described below. The confirmation screen is a screen displayed on the monitor 928 after photography, by which the inspector checks whether or not there is no defect in the photographed tomographic image. In addition, the lesion or the like can be roughly checked for determination of the part to be concerned in the next photography.

Reference numeral 2201 denotes a display screen for a two-dimensional fundus image obtained by the fundus observation CCD 172; 2202, a tomographic image display screen for checking the acquired tomographic image; and 2203, a screen for displaying a fundus image reconstructed from the acquired tomographic images (hereinafter referred to as a C-scan screen). In addition, reference numeral 2211 denotes a slider for specifying a section position of the tomographic image displayed on the tomographic image display screen. Further, reference numeral 2213 denotes an NG button to be clicked by the mouse or the like when the inspector determines that the acquired tomographic image has a defect, and reference numeral 2214 denotes an OK button to be clicked by the mouse or the like when the inspector determines that the acquired tomographic image is a good image without a defect.

In the two-dimensional fundus image display screen 2201, there are displayed a tomographic image acquiring range 2221 and an arrow 2222 indicating a position and a scan direction in the tomographic image acquiring range of the tomographic image displayed on the tomographic image display screen 2202. Similarly, also in the C-scan screen 2203, there is displayed an arrow 2232 indicating a position and a scan direction in the tomographic image acquiring range of the tomographic image displayed on the tomographic image display screen 2202.

In the initial state of this screen, the tomographic image display screen 2202 displays the tomographic image at the center position in the tomographic image acquiring range 2221. In order to check each of the tomographic images in more detail, the inspector operates the slider 2211. By this operation, the tomographic image displayed on the tomographic image display screen 2202 moves in the tomographic image acquiring range. Thus, the inspector can check all the tomographic images. In this way, the inspector can precisely check whether or not the image has a defect and can roughly check the lesion or the like.

(Operational Flow)

Figure 1C:
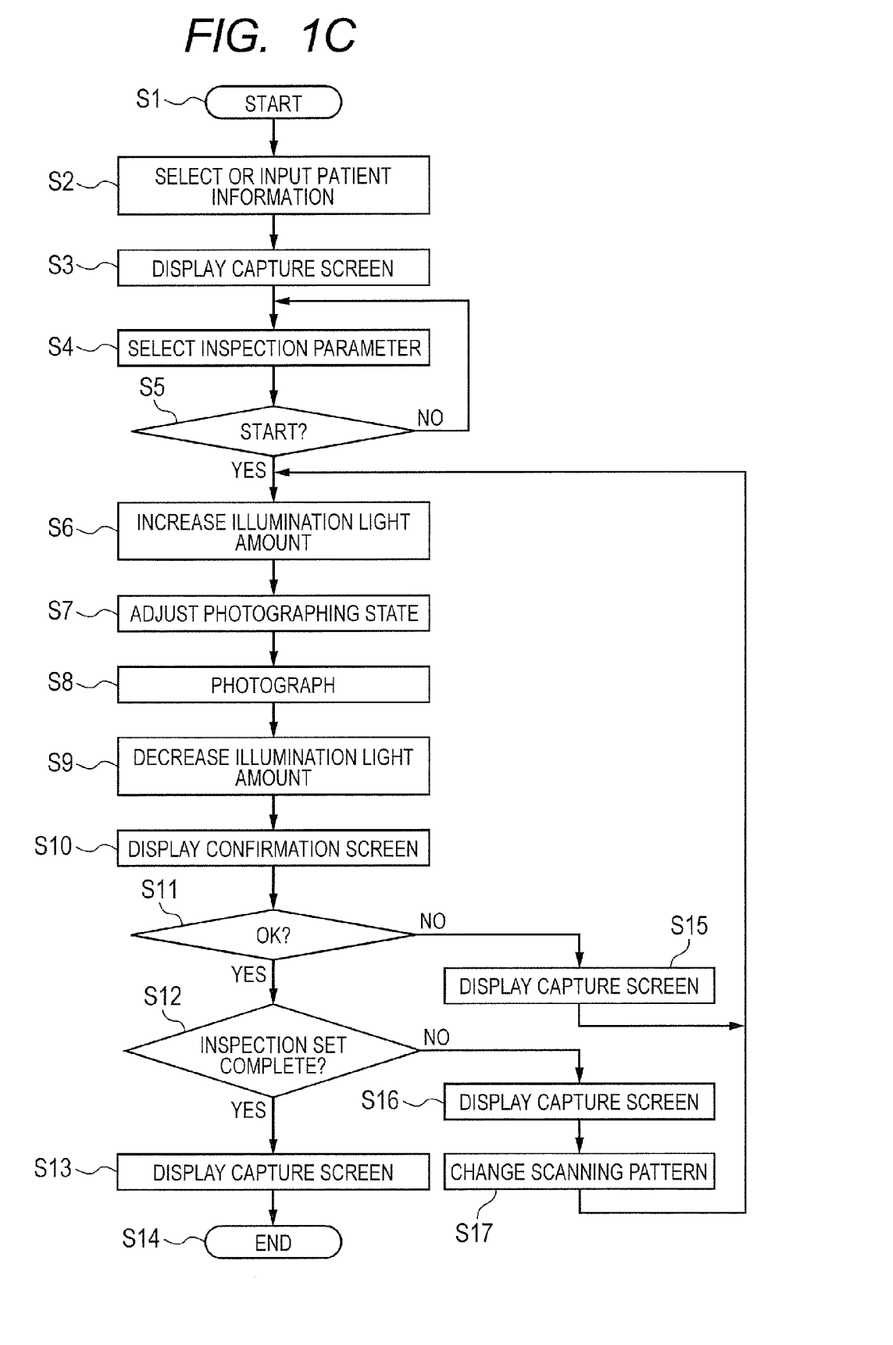
FIG. 1C is an explanatory diagram of an operational flow according to the first embodiment.

An operational flow of the photography in this embodiment is described with reference to FIG. 1C. First, when the inspection is started in Step S1, the personal computer 925 executes an inspection program, and a patient information input screen is displayed on the monitor 928 in Step S2. The inspector selects the patient or inputs patient information in a case of a new patient. In accordance with an inspector's operation (such as mouse clicking of the OK button displayed on the patient information input screen), the process proceeds to Step S3. In Step S3, the monitor 928 displays a capture screen 1000 described above and waits for an inspector's input of an inspection parameter.

In Step S4, the inspector clicks each button on the capture screen 1000 in the state waiting for the input of the inspection parameter, so as to select the left or right eye to be inspected and the inspection set. When the inspector selects (clicks) the start button 1004 as an input unit in Step S5, the process proceeds to Step S6. When the selection is not performed, the process returns to the state still waiting for the input of the inspection parameter (Step S4).

In Step S6, the personal computer 925 is caused to function as an increasing unit for increasing a measurement light amount so that the measurement light amount is increased. Thus, the eye to be inspected can be photographed. Specifically, the OCT scanner 134 starts to scan based on the scan pattern prepared in an inspection set memory unit of the personal computer 925 in advance, which corresponds to the inspection set selected in Step S4. In other words, the inspection set memory unit corresponds to an example of a memory unit for storing control information for causing a first control unit to control a scanning unit to sequentially perform a first scan and a second scan after the first scan. In addition, the OCT light source 101 increases a light emission amount from a decreased light amount or an off-state to a level enabling the photography. Then, the OCT shutter 140 is retreated from the optical path. Thus, it is possible to allow the measuring light to enter the eye to be inspected at a level enabling the photography. After Step S6, the process proceeds to Step S7.

In Step S7, previews of the acquired image of the fundus of the eye to be inspected and the acquired tomographic image are displayed on the capture screen 1000 as a first screen on the monitor 928 as a real-time image (moving image) that is a first display. Then, based on those pieces of information, various adjustments are performed so that an optimal photographing state can be obtained. Specifically, based on the image of the anterior segment of the eye to be inspected, which is obtained by the anterior segment observation CCD 171, X, Y, and Z adjustments are performed so that an inspection portion becomes an optimal position with respect to the eye to be inspected.

In addition, at the same time, the optical path length adjustment of the reference optical path by moving the reference mirror 132-4, the focus adjustment of the fundus image by the lens 135-3, and the focus adjustment of the tomographic image by the lens 135-5 are performed. Thus, the state of the apparatus can be set to an optimal state for photographing the eye to be inspected. After the adjustments are completed in this step, the process proceeds to Step S8. Here, the process proceeds to Step S8 when the inspector uses the mouse to click the photography button 1003 on the capture screen 1000 described above or automatically when the various adjustments are completed.

In Step S8, the tomographic image is photographed by the scan pattern based on the inspection set that is set in Step S4. At the same time, a storage device in the personal computer 925 stores the tomographic image and the fundus image acquired by the fundus observation CCD. After that, the process proceeds automatically to Step S9. In Step S9, because the photography is already completed, the personal computer 925 is caused to function as a reducing or eliminating unit for reducing or eliminating the measurement light amount, to thereby decrease or eliminate the light entering the subject. Specifically, the OCT shutter 140 is inserted in the optical path, and the OCT light source 101 is turned off or the light emission amount is decreased or eliminated. In other words, the personal computer 925 corresponds to an example of a second control unit for reducing the light amount irradiated to the eye to be inspected after finishing the first scan and before the second scan, which are performed based on the control information.

In addition, the operation of the OCT scanner 134 is stopped at an arbitrary position. After that, the process proceeds automatically to Step S10. Here, instead of stopping the OCT scanner 134, it is possible to drive the OCT scanner 134 in a state where the scan speed is reduced. Thus, unnecessary drive power can be reduced, and unnecessary drive noise can also be reduced. In Step S10, the monitor displays the above-mentioned confirmation screen 2000 as a second screen, and the tomographic image as a still image of a second display is displayed on the monitor.

Here, as described above, the inspector checks each tomographic image to determine whether or not the image has a defect while considering the presence or absence of lesion and which part is to be concerned in the next photography. This determination may take a long time period. Therefore, by reducing the light amount irradiating the subject in Step S9, the load on the subject can be reduced. Note that, the order between Step S9 and Step S10 may be opposite.

This point is described below in detail. If the apparatus includes a first monitor for displaying a real-time observation image (moving image) before acquiring an image and a second monitor for displaying the acquired image (still image) after acquiring the image, the fundus of the eye to be inspected is always irradiated also in a time period for changing a scan pattern to the next scan pattern in the conventional configuration. This is because it is preferred that the real-time observation image (moving image) can always be observed on the first monitor. In contrast, in this embodiment, the same monitor performs a time-sharing display in which the capture screen 1000 as the first screen and the confirmation screen 2000 as the second screen are switched.

Therefore, when the confirmation screen 2000 is displayed, it is not necessary to irradiate the fundus of the eye to be inspected, and hence the load on the subject can be reduced by decreasing the irradiation light amount. In addition, by automatically performing this, the load on the inspector can be reduced.

Next, the process proceeds to Step S11, in which the inspector performs a selection input with respect to whether or not the tomographic image has a defect. When the tomographic image has no defect, the inspector makes a mouse click of the above-mentioned OK button 2214 on the confirmation screen 2000, and the process proceeds to Step S12. On the other hand, when the image has a defect, the NG button 2213 is clicked, and the process proceeds to Step S15.

When the process proceeds to Step S15, the screen to be displayed on the monitor is switched from the confirmation screen to the capture screen, and the process returns to Step S6. In this way, the content of the display on the single monitor 928 is appropriately and automatically switched in a time-sharing manner to be suitable for the situation, and hence the inspector can perform a comfortable operation even on a single monitor. In addition, because even the single monitor can display a large acquired image of the eye to be inspected on the monitor, it is possible to perform the adjustment operation and the image check easily.

In Step S12, it is determined whether or not all the scan patterns stored in the inspection set that is set in the Step S4 are completed. When all the scan patterns to be inspected are completed, the process proceeds to Step S13. On the other hand, when there remains a scan pattern to be inspected, the process proceeds to Step S16. When the process proceeds to Step S16, the display unit 928 automatically switches the screen display from the confirmation screen 2000 to the capture screen 1000 as a third screen, and the process proceeds to Step S17.

In Step S17, the scan control unit reads out the next scan pattern determined in advance in the inspection set selected in Step S4, and sets the read scan pattern as the scan pattern for the next scan by the OCT scanner 134. After that, the process returns to Step S6, in which the OCT scanner 134 automatically starts the scan based on the scan pattern set in Step S17. In addition, the personal computer 925 is caused to function as an increasing unit for increasing the measurement light amount. Then, the OCT light source 101 is turned on, the light amount is increased up to a level enabling the photography or higher, and the OCT shutter 140 is retreated from the optical path.

When the scan patterns stored in the inspection set are all completed, the process proceeds to Step S13 in which the screen display is switched from the confirmation screen 2000 to the capture screen 1000. After that, the inspection is completed in Step S14. The photography flow of this embodiment is as described above.

As a method for increasing and decreasing the light amount irradiated to the subject in Steps S6 and S9, the increase/decrease of the measuring light and the retreat/insertion of the shutter are performed, but this is not a limitation.

For instance, there is a method of increasing and decreasing the irradiation light amount only by the increase/decrease of the measuring light. In this case, it is not necessary to constitute the shutter in the optical system. Therefore, because the irradiation light amount to the subject can be decreased by a simple configuration, cost can be reduced.

In addition, there is also a method of increasing and decreasing the irradiation light amount only by the retreat/insertion of the OCT shutter 140. By using this method, it is possible to certainly perform physical block of light by the shutter (elimination of light amount irradiating the test object).

Further, there is a method of setting a mirror angle of the OCT scanner 134 to an angle deviating from the optical path guided to the subject so as to increase and decrease the irradiation light amount. According to this method, it is not necessary to constitute the shutter in the optical system, and it is possible to certainly perform physical block of light.

(Modified Example of Flow)

Figure 3A:
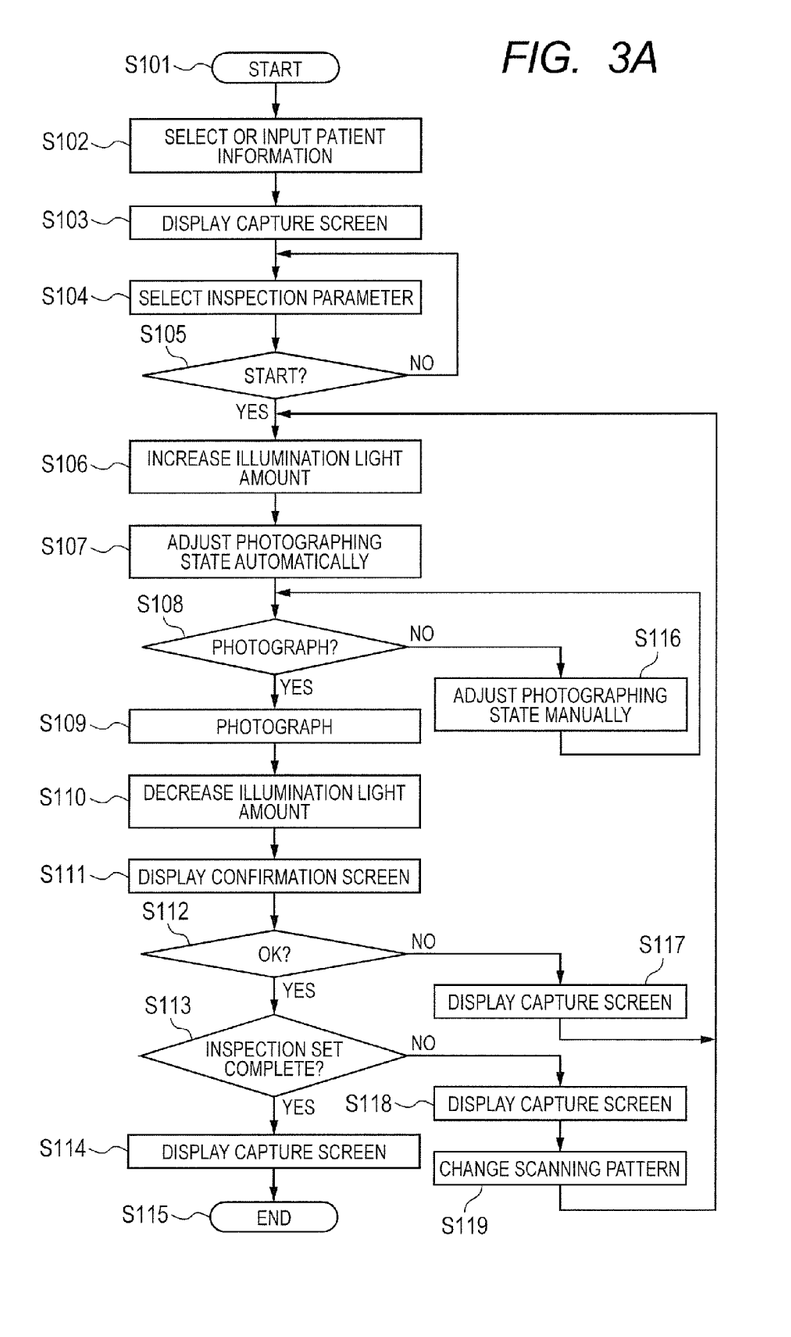
FIG. 3A is a diagram illustrating an operational flow in which automatic adjustment is added so as to automatically obtain an optimal photographing state based on the acquired image.
Figure 3B:
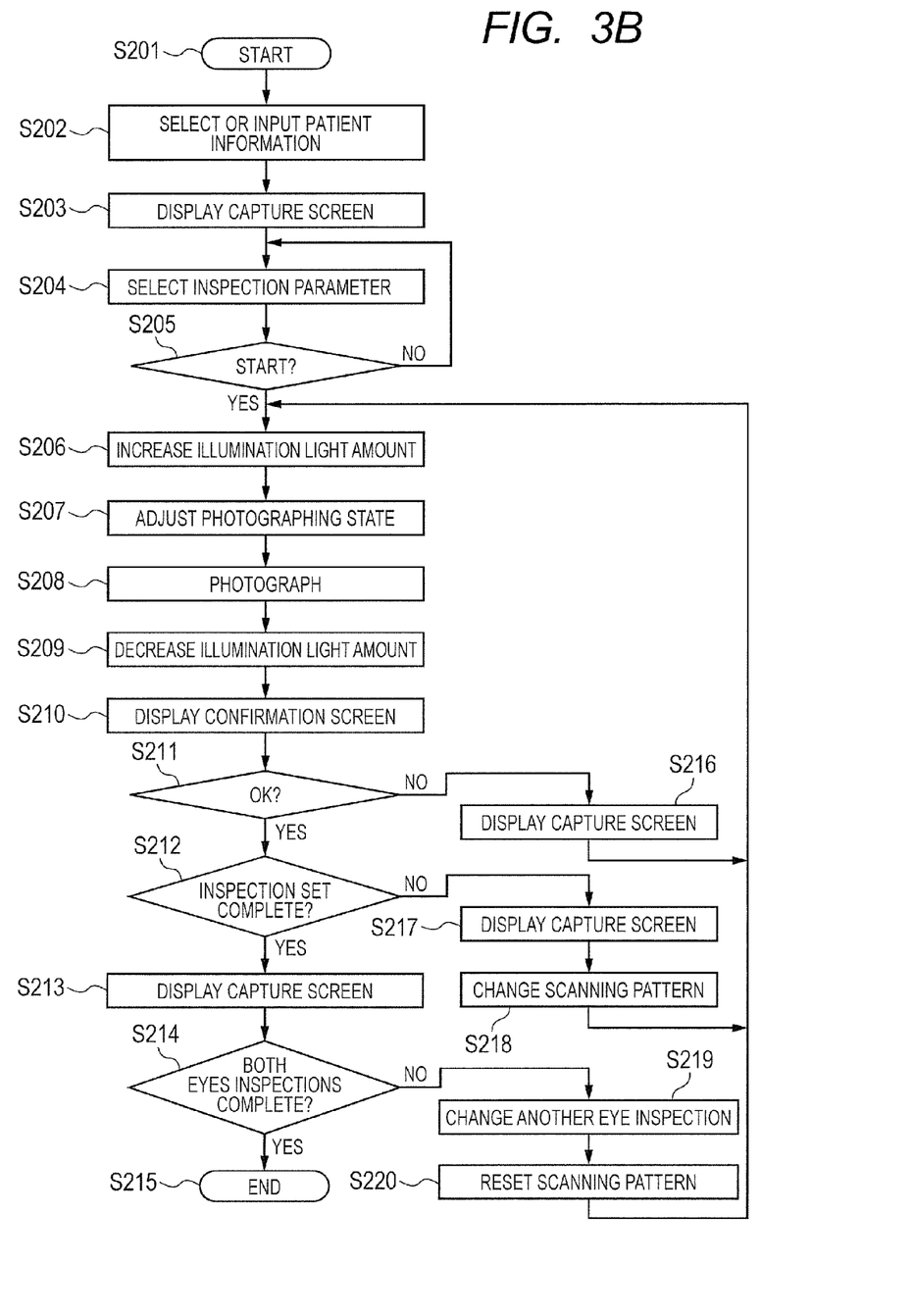
FIG. 3B is a diagram illustrating an operational flow in which switching between both eyes is added.
Figure 3C:
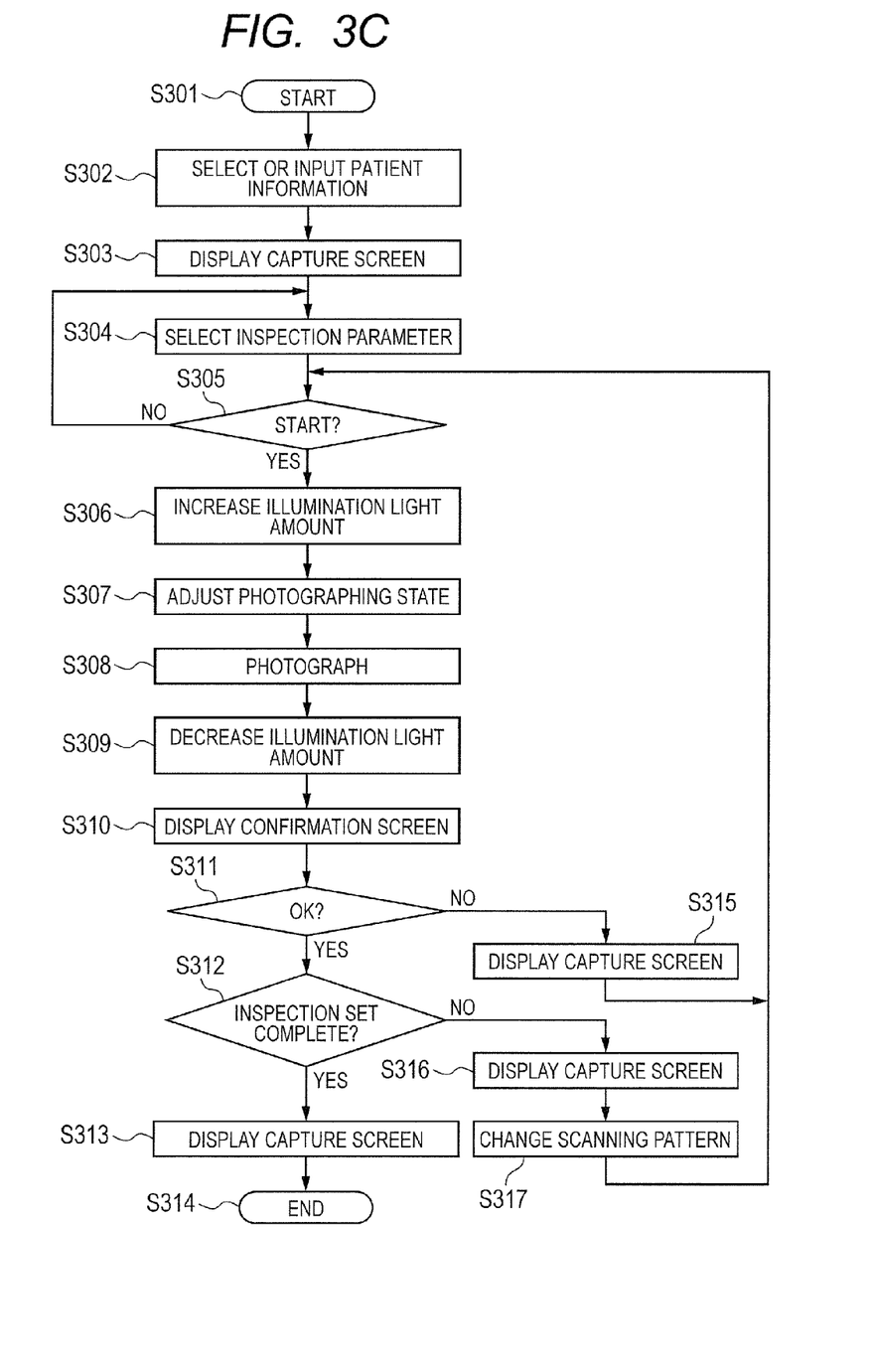
FIG. 3C is a diagram illustrating an operational flow in which a light amount irradiating a test object is increased up to a level that enables to acquire an image not automatically but by an inspector's input when detecting the start of acquiring the next image.

Next, with reference to FIGS. 3A to 3C, a modified example of the above-mentioned flow is described. FIG. 3A is an operational flow in which the automatic adjustment is added to the above-mentioned operational flow. Steps S101 to S106 are the same as the above-mentioned steps, and hence description thereof is omitted. In Step S107 after increasing the measuring light up to a level enabling the photography, various adjustments are automatically performed so that an optimal photographing state can be obtained based on the acquired anterior segment observation image, two-dimensional fundus image, and tomographic image. Specifically, based on information of the anterior segment observation image, the stage portion 950 is automatically driven and controlled so that the inspection portion comes to an optimal position with respect to the eye to be inspected.

In addition, based on information of the tomographic image, the reference mirror 132-4 is automatically driven and controlled so that the optical path length adjustment of the reference optical path is performed. At the same time, the lens 135-3 and the lens 135-5 are automatically driven and controlled so as to make focus of the fundus image and the tomographic image. Thus, the state of the apparatus is automatically made to be an optimal state for photography of the eye to be inspected. After that, the process proceeds to Step S108. In Step S108, the inspector sees the image adjusted in Step S107 and selects whether or not to perform the photography in this adjusted state. In the case of performing the photography, the inspector selects the photography button 1003 displayed on the capture screen 1000 by a mouse or the like, and the process proceeds to Step S109.

On the other hand, in Step S108, when the inspector sees the image adjusted in Step S107 and the inspector determines that further adjustment is necessary, the process proceeds to Step S116. In Step S116, the photographing state is adjusted by an inspector's operation. Specifically, the inspector sees the capture screen 1000 and clicks an input portion disposed in the display screen of the anterior segment observation image display screen 1101, so as to adjust X and Y positions. In addition, the sliders 1103, 1203, and 1302 are moved to slide so as to perform Z position adjustment, focus adjustment, and coherence gate adjustment. When a state enabling photography is obtained by the above-mentioned manual adjustments, the input for photography is performed in Step S108, and the process proceeds to Step S109.

From Step S109 for the photography to Step S115 for the end (including Steps S117 to S119) are the same as those in the above-mentioned operational flow, and hence description thereof is omitted. According to the above-mentioned flow, automatic adjustment can be performed along with an automatic increase of the irradiation light amount. Therefore, it is possible to reduce operation required to the inspector so that ease of operation can be improved.

Next, with reference to FIG. 3B, description is given of an operational flow to which the switching between both eyes is added. From Step S201 to Step S212 in which it is determined whether or not the scan condition for one eye stored in advance has been completed (including Steps S216 to S218) are the same as those in the above-mentioned operational flow, and hence description thereof is omitted.

In this operational flow, the photography by the last scan pattern of the inspection set is performed, and the capture screen is displayed. After that, in Step S214, it is determined whether or not inspections of both eyes have been completed. When it is determined in Step S214 that the inspections of both eyes have not been completed, that is, when the inspection of the other eye which is not the eye currently inspected, is to be performed next, the process proceeds to Step S219.

In Step S219, in order to position the inspection portion for the other eye which is not the eye currently inspected, the stage portion 950 is driven and controlled based on position information of a standard eye stored in the personal computer 925 in advance. After that, the process proceeds to Step S220. In Step S220, the scan pattern is reset to be the initial state for the subsequent inspection. Thus, the inspection can be started by the initial scan pattern in the inspection set selected in Step S204 also for the other eye to be inspected. After that, the process returns to Step S206, in which the irradiation light amount is automatically increased.

When the process proceeds to Step S214 in the state where the inspection of both eyes is completed, the process proceeds to Step S215 to complete the inspection. In this way, by automatically switching between both eyes, a measurement time period can be shortened so that a through-put can be improved.

In the above-mentioned operational flow, the scan pattern is switched, and the irradiation light amount is automatically increased when the measurement is restarted, but this is not a limitation. The example thereof is described with reference to FIG. 3C. The operational flow illustrated in FIG. 3C is different from that illustrated in FIG. 1C in the step to which the process proceeds after Step S17. In the operational flow of FIG. 1C, the process returns to Step S6 after Step S17 to increase the irradiation light amount automatically. On the other hand, in this operational flow, the process returns to Step S305 after Step S317 to request the inspector to perform an operation regarding whether or not to start to increase the scan light amount.

Thus, the irradiation of the subject with the measuring light is started by a subject's positive operation, and hence it is possible to adjust to an inspector's inspection timing, and it is possible to further decrease the light amount irradiating the subject.

In the above description, as a method of increasing and decreasing the light amount irradiating the subject, only the measuring light for acquiring the tomographic image is paid attention to, but this is not a limitation. For instance, fundus observation illumination light as measuring light for acquiring the two-dimensional fundus image may also be increased and decreased similarly so that the irradiation light amount can be further decreased. This is described in a second embodiment. In addition, because the anterior segment observation illumination light is weak visible light, the anterior segment observation illumination light may be continuously emitted, but it is possible to increase and decrease simultaneously with the increase and decrease of the measuring light.

The ophthalmologic apparatus is exemplified and described in this embodiment, but this is not a limitation. It is possible to embody the present invention in other photography apparatus, for example, an endoscope. Therefore, the test object is not limited to the eye, and it is possible to embody the present invention also for skin.

Second Embodiment

Figure 4A:
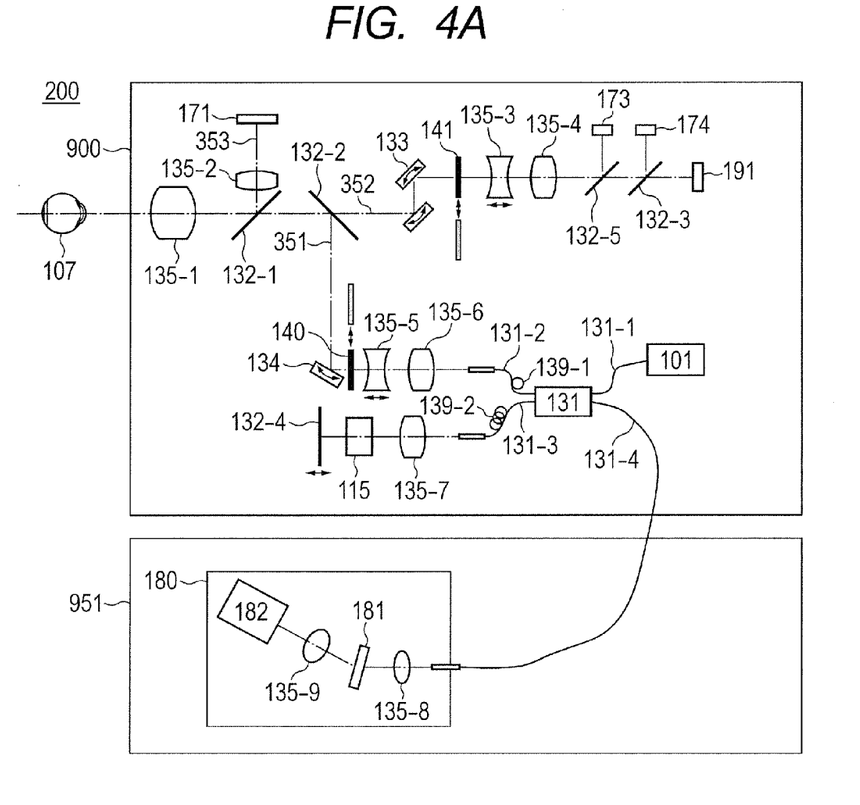
FIG. 4A is an explanatory diagram of a measurement optical system of an image acquiring portion of the ophthalmologic apparatus.
Figure 4B:
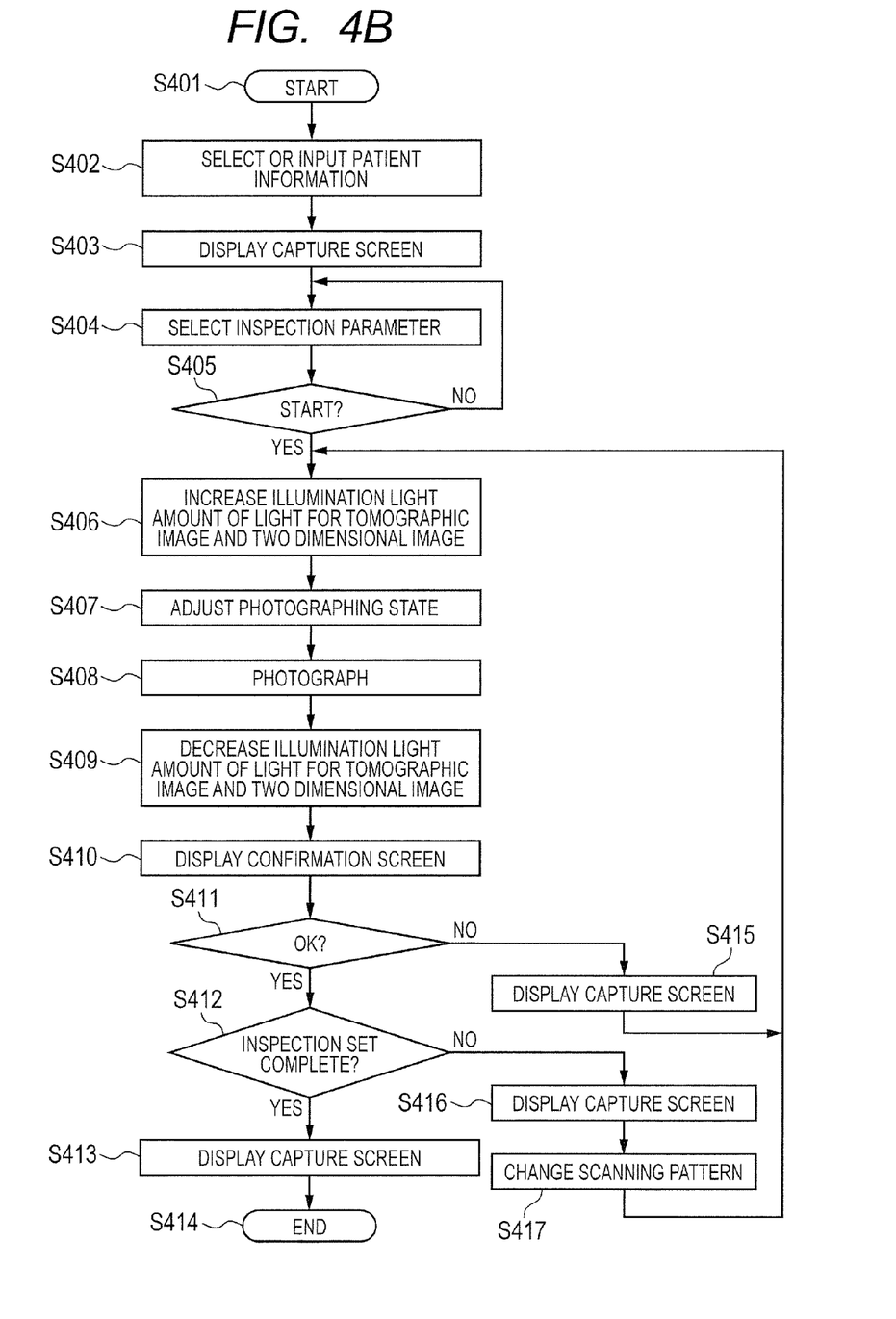
FIG. 4B is an explanatory diagram of an operational flow thereof.

In this embodiment, description is given of a case where an SLO is used for acquiring a two-dimensional image. With reference to FIGS. 4A and 4B, an optical system and an operational flow according to this embodiment are described. Here, only a changed point of the optical system and the operational flow is described, and description of other portions is omitted. FIG. 4A illustrates the optical system according to this embodiment. Here, only a difference from the first embodiment is described, and other portions are omitted.

Similarly to the first embodiment, the optical path 352 includes the third dichroic mirror 132-3, the lenses 135-3 and 135-4, and the fixation lamp 191. Other than that, this embodiment includes an SLO light source 174, a mirror 132-5, a photodiode 173, an SLO scanning unit 133, and an SLO shutter 141. The SLO light source 174 emits light having a wavelength of around 780 nm. The mirror 132-5 is a mirror with a hole or a prism on which a hollow mirror is evaporated, and separates illumination light of the SLO light source 174 from return light from the fundus. The photodiode 173 detects the return light from the fundus.

The SLO scanning unit 133 scans the fundus of the eye to be inspected 107 with light emitted from the SLO light source 174, and is constituted of an X scanner for scanning in an X direction and a Y scanner for scanning in a Y direction. In this embodiment, the X scanner is constituted of a polygon mirror for performing high speed scan. The SLO shutter 141 can be inserted (return) in the optical path 352 or retreated from the optical path 352 by a drive unit (not shown). In other words, in order to decrease or eliminate the light amount irradiating the test object, the scan range of the scanning unit is retreated from the optical path guided to the test object. In other words, by causing the first unit to control the scanning unit so that the scanning light from the scanning unit does not irradiate the eye to be inspected, the light amount irradiating the eye to be inspected is decreased. In addition, in order to increase the light amount irradiating the test object, the scan range of the scanning unit is reset in the optical path guided to the test object. In other words, by causing the first unit to control the scanning unit so that the scanning light from the scanning unit irradiates the eye to be inspected, the light amount irradiating the eye to be inspected is increased.

According to the configuration described above, by observing the fundus of the eye to be inspected, a two-dimensional fundus image with high contrast can be acquired even if near infrared light is used.

(Operational Flow)

Next, the operational flow according to this embodiment is described with reference to FIG. 4B. Here, only Steps S406 and S409 as a difference from the first embodiment are described, and description of the other steps is omitted.

In this operational flow, the irradiation light amount of the two-dimensional image photography light for acquiring the two-dimensional fundus image (SLO light) is also increased simultaneously with the increase in irradiation light amount of the measuring light for acquiring the tomographic image in Step S406. Specifically, the SLO scanner 133 is driven, the light amount emitted from the SLO light source 174 is controlled to be increased, and the SLO shutter 141 is retreated from the optical path.

In addition, in Step S407 after the photography, the irradiation light amount of the measuring light is decreased, and simultaneously the two-dimensional image photography light is also decreased. Specifically, the SLO shutter 141 is inserted in the optical path to control and decrease the light amount emitted from the SLO light source 174. In addition, the SLO scanner 133 is stopped at an arbitrary position.

Here, as a method of increasing and decreasing the irradiation light amount of the two-dimensional image photography light, the increase/decrease of the light emission amount of the SLO light source 174 and the retreat/insertion of the SLO shutter 141 are performed, but this is not a limitation. For instance, there is a method of increasing and decreasing the irradiation light amount only by controlling the light emission amount of the SLO light source 174 to be increased or decreased. In this case, it is not necessary to constitute the shutter in the optical system. Therefore, the irradiation light amount to the subject can be decreased by a simple configuration, and hence cost can be reduced.

In addition, there is a method of increasing and decreasing the irradiation light amount only by the retreat/insertion of the SLO shutter 141. By using this method, it is possible to certainly perform physical block of light by the shutter. Further, there is a method of increasing and decreasing the irradiation light amount by setting an angle of the SLO scanner 133 to an angle deviating from the optical path guided to the subject. According to this method, it is not necessary to constitute the shutter in the optical system, and it is possible to certainly perform physical block of light.

By using the configuration and the operational flow as described above, it is possible to provide an ophthalmologic apparatus that can obtain the two-dimensional observation image with high contrast by SLO and can decrease the light amount irradiating the subject.

Third Embodiment

In this embodiment, the measurement light amount is increased and decreased without a screen change on the monitor, namely without confirmation on the display unit. An operational flow according to this embodiment is described with reference to FIG. 5. First, the inspection is started in Step S501, and then the process proceeds to Step S502. In Step S502, the inspector selects the inspection set appropriate for inspection of the test object.

Figure 5:
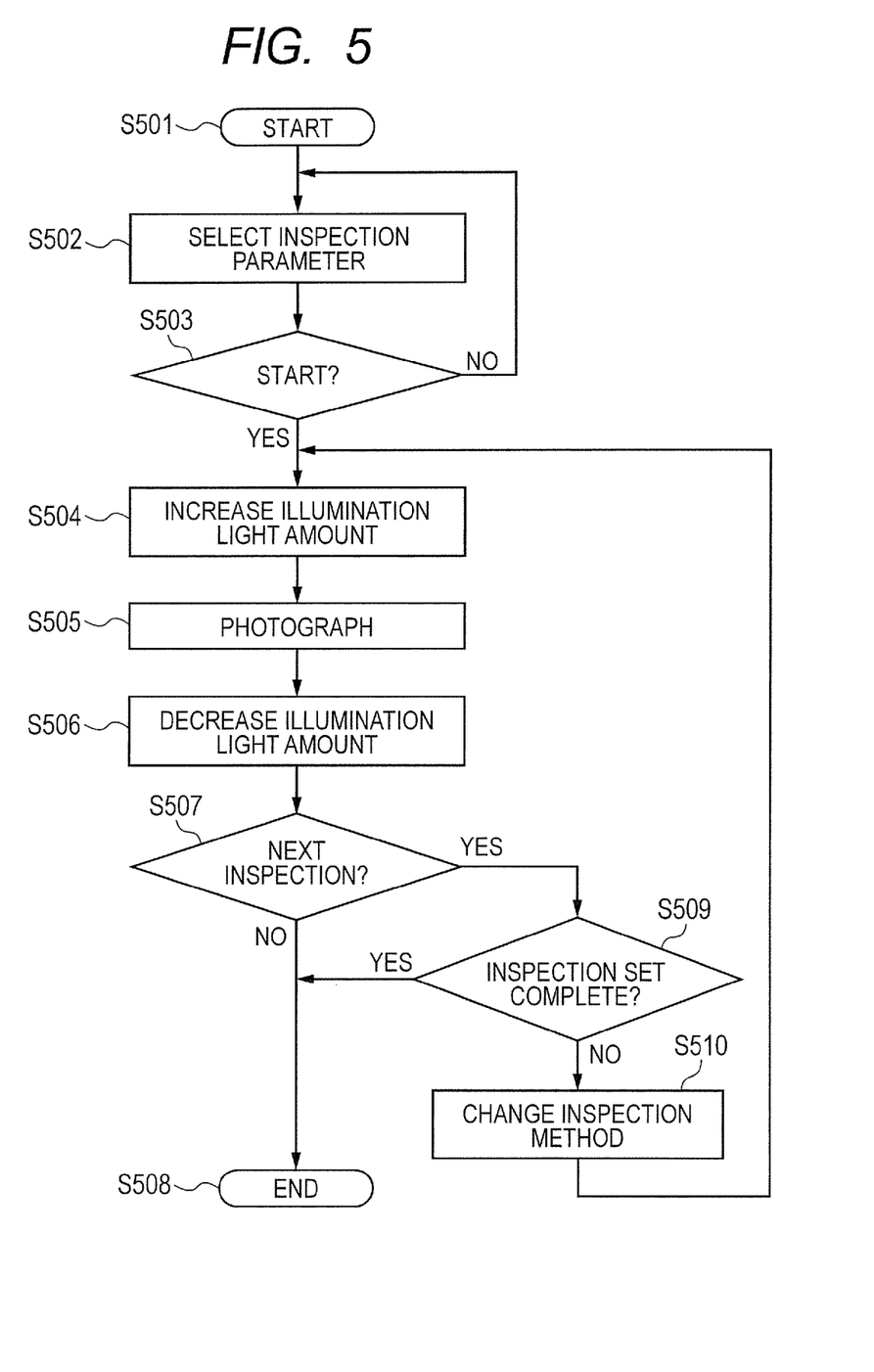
FIG. 5 is an explanatory diagram of an operational flow according to a third embodiment.

Here, the inspection set means a set of a plurality of acquiring methods for acquiring different pieces of information from the test object, the methods being ordered and stored. The acquiring method means, for example, the above-mentioned scan pattern. By scanning the test object by different scan patterns, different pieces of information of the test object can be obtained. The inspection set may be selected by the input unit such as a button (not shown) disposed in advance on the apparatus or may be input on the above-mentioned capture screen. After the inspector finishes selection of the inspection set in this step, the process proceeds to Step S503.

In Step S503, the inspector selects whether or not to increase the measurement light amount irradiating the test object up to a level enabling the photography or higher. When the inspector selects not to increase the measurement light amount, it becomes a waiting state. The selection in this case may also be performed by the input unit such as a button (not shown) disposed in advance on the apparatus or by input on the above-mentioned capture screen. When the inspector selects to increase the measuring light in this step, the process proceeds to Step S504.

In Step S504, the measurement light amount irradiating the test object is automatically increased. Thus, tomographic information of the test object can be obtained. The method of increasing the measurement light amount is described above in the first embodiment, and hence description thereof is omitted. In addition, it is possible to use the acquired tomographic image of the test object for performing various adjustments of the photographing state, for example, alignment adjustment, focus adjustment, and reference optical path length adjustment. In this case, instructions of the various adjustments may be input by the input unit such as a button (not shown) disposed in advance on the apparatus or may be input on the above-mentioned capture screen.

The process proceeds to Step S505 when the inspector operates the input unit such as the photography button (not shown) disposed in advance on the apparatus in the previous step. In addition, the process may proceed to Step S505 by input on the above-mentioned capture screen or automatically when the various adjustments are completed.

In Step S505, the tomographic image is photographed based on the acquiring method based on the inspection parameter set in Step S502, and simultaneously the tomographic image is stored in the storage device of the personal computer 925. After that, the process automatically proceeds to Step S506.

In Step S506, the measurement light amount irradiating the test object is decreased or eliminated. Thus, a total light amount irradiating the test object can be decreased, and hence a low-invasive photography apparatus can be realized. The method of decreasing the measurement light amount is described above in the first embodiment, and therefore description thereof is omitted. After that, the process proceeds to Step S507.

In Step S507, the inspector determines whether or not to change to the next scan pattern. When the inspector selects to change to the next inspection method, the process proceeds to Step S509. When the inspector selects not to change, the process proceeds to S508. The selection in this case may be performed by the input unit such as a button (not shown) disposed in advance on the apparatus or may be input on the above-mentioned confirmation screen. In addition, it is possible to automatically proceed to the next step. For instance, a timer that counts time after photography may be disposed in the personal computer 925, and the process may automatically proceed to Step S509 when a predetermined time period has passed after the photography.

In Step S509, it is automatically determined whether or not inspections by the plurality of acquiring methods stored in the inspection set in advance have all been completed. When all the inspections have been completed, the process proceeds to Step S508. On the other hand, when there remains an inspection by another acquiring method, the process proceeds to Step S510.

In Step S510, the next acquiring method determined in advance in the inspection set selected in Step S502 is transferred to the personal computer 925 as the control portion, and the control portion prepares for the next inspection. After that, the process returns to Step S504, and the measurement light amount irradiating the test object is automatically increased. When the process proceeds to Step S508, the inspection is completed.

According to the operational flow described above, when performing a plurality of inspections of the test object, the automatic switching among the plurality of inspections and the accompanying automatic increase and decrease of the irradiation light amount can be realized without a screen display.

Modified Example 1

In the embodiment described above, the light amount irradiating the test object is not changed in the individual scan conditions when the image is acquired. However, it is possible to change the light amount irradiating the test object in the individual scan conditions (different scan patterns and different scan ranges) when the image is acquired.

Modified Example 2

In the embodiment described above, the light amount irradiating the test object is increased by the inspector's input when the monitor as the display unit displays the capture screen. However, it is possible to increase the light amount irradiating the test object automatically without the inspector's input.

Other Embodiments

In addition, the present invention can be realized also by performing the following process. Specifically, software (program) for realizing the functions of the above-mentioned embodiments is supplied to a system or an apparatus via a network or various storage media, and a computer (CPU, MPU, or the like) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-012845, filed Jan. 25, 2012, which is hereby incorporated by reference herein in its entirety.

What is claimed is:

1. An ophthalmologic apparatus, comprising:
a first control unit which controls a scanning unit configured to scan an eye to be inspected with light emitted from a light source;
a memory unit which stores control information for causing the first control unit to control the scanning unit to sequentially perform a first scan for obtaining a first image of the eye to be inspected and a second scan for obtaining a second image of the eye to be inspected after the first scan; and
a second control unit which decreases the amount of light irradiating the eye to be inspected or prevents the irradiation of the eye to be inspected with the light from the light source after finishing the first scan and before starting the second scan, which are performed based on the control information.

2. An ophthalmologic apparatus according to claim 1, wherein the second control unit increases the amount of light irradiating the eye to be inspected when the second scan is performed based on the control information.

3. An ophthalmologic apparatus according to claim 2, wherein the first image and the second image are tomographic images of the fundus of the eye to be inspected.

4. An ophthalmologic apparatus according to claim 2, further comprising a display control unit which controls a display unit to display an image of the eye to be inspected obtained based on return light from the eye to be inspected scanned with light from the scanning unit,
wherein the display control unit controls the display unit to display a moving image of the eye to be inspected obtained from the return light before the first scan, and switches the display after the first scan from the moving image of the eye to be inspected to a still image of the eye to be inspected obtained by the first scan as the first image.

5. An ophthalmologic apparatus according to claim 1, further comprising a display control unit which controls a display unit to display an image of the eye to be inspected obtained based on return light from the eye to be inspected scanned with light from the scanning unit,
wherein the display control unit controls the display unit to display a moving image of the eye to be inspected obtained from the return light before the first scan, and switches the display after the first scan from the moving image of the eye to be inspected to a still image of the eye to be inspected obtained by the first scan as the first image.

6. An ophthalmologic apparatus according to claim 3, wherein the first image and the second image are tomographic images of the fundus of the eye to be inspected.

7. An ophthalmologic apparatus according to claim 1, wherein the second control unit decreases the amount of light emitted from the light source so as to decrease the amount of light irradiating the eye to be inspected or prevents the irradiation of the eye to be inspected with light from the light source.

8. An ophthalmologic apparatus according to claim 1, further comprising a restriction unit that is insertable and removable to and from an optical path connecting the light source and the eye to be inspected,
wherein the second control unit inserts the restriction unit in the optical path so as to decrease the amount of light irradiating the eye to be inspected or prevent the irradiation of the eye to be inspected with light from the light source.

9. An ophthalmologic apparatus according to claim 1, wherein the second control unit controls the first control unit to control the scanning unit so that scanning light from the scanning unit does not irradiate the eye to be inspected, to thereby decrease the amount of light irradiating the eye to be inspected or prevent the irradiation of the eye to be inspected with light from the light source.

10. An ophthalmologic apparatus according to claim 1, wherein the first control unit decreases the scan speed of the scanning unit when the second control unit decreases the amount of light irradiating the eye to be inspected or prevents the irradiation of the eye to be inspected with the light from the light source.

11. An ophthalmologic apparatus according to claim 1, wherein the first scan and the second scan have different scan patterns or different scan ranges.

12. An ophthalmologic apparatus according to claim 11, wherein in each of the first scan and the second scan, the light emitted from the light source is scanned on a line on the fundus of the eye to be inspected.

13. An opthalmologic apparatus according to claim 11, wherein in each of the first scan and the second scan, the light emitted from the light source is linearly scanned on the fundus of the eye to be inspected.

14. An ophthalmologic apparatus according to claim 1, wherein the first image and the second image are tomographic images of the fundus of the eye to be inspected.

15. An ophthalmologic apparatus according to claim 1, further comprising an image forming unit which forms an image of the eye to be inspected based on return light from the eye to be inspected scanned with light from the scanning unit,
wherein the image forming unit forms the first image based on the return light from the eye to be inspected scanned as the first scan, and forms the second image based on the return light from the eye to be inspected scanned as the second scan.

16. An ophthalmologic apparatus according to claim 1, further comprising an image forming unit which forms an image of the eye to be inspected based on return light from the eye to be inspected scanned with light from the scanning unit,
wherein the image forming unit forms the first image based on the return light from the eye to be inspected scanned as the first scan, and forms the second image based on the return light from the eye to be inspected scanned as the second scan, and
wherein the second control unit increases the amount of light irradiating the eye to be inspected after forming the first image by the image forming unit and before starting the second scan, which are performed based on the control information.

17. An ophthalmologic apparatus according to claim 1, wherein in each of the first scan and the second scan, the light emitted from the light source is scanned on a line on the fundus of the eye to be inspected.

18. An ophthalmologic apparatus according to claim 1, wherein in each of the first scan and the second scan the light emitted from the light source is linearly scanned on the fundus of the eye to be inspected.

19. An ophthalmologic control method, comprising:
a scan step of performing a first scan for obtaining a first image of the eye to be inspected based on control information for controlling a scanning unit for scanning an eye to be inspected with light emitted from a light source to sequentially perform the first scan and a second scan for obtaining a second image of the eye to be inspected after the first scan; and
a light amount decreasing step of decreasing the amount of light irradiating the eye to be inspected after finishing the first scan and before starting the second scan.

20. A non-transitory recording medium having a program recorded thereon, the program causing a computer to execute:
a scan step of performing a first scan for obtaining a first image of the eye to be inspected based on control information for controlling a scanning unit for scanning an eye to be inspected with light emitted from a light source to sequentially perform the first scan and a second scan for obtaining a second image of the eye to be inspected after the first scan; and
a light amount decreasing step of decreasing the amount of light irradiating the eye to be inspected after finishing the first scan and before starting the second scan.

* * * * *